United States Patent [19]

Pretorius et al.

[11] 4,208,284
[45] Jun. 17, 1980

[54] APPARATUS FOR DISTRIBUTION SEPARATION PROCESSES

[76] Inventors: Victor Pretorius, 37 Eridanus St., Waterkloof, Pretoria; Hans H. Hahn, 38 Marais St., Bailey's Muckleneuk, Pretoria, both of South Africa

[21] Appl. No.: 884,511

[22] Filed: Mar. 8, 1978

Related U.S. Application Data

[63] Continuation of Ser. No. 700,891, Jun. 29, 1976, abandoned, which is a continuation of Ser. No. 423,710, Dec. 11, 1973, abandoned, which is a continuation-in-part of Ser. No. 86,621, Nov. 3, 1970, Pat. No. 3,796,657, which is a continuation of Ser. No. 598,365, Dec. 1, 1966, abandoned, which is a continuation-in-part of Ser. No. 548,900, May 10, 1966, Pat. No. 3,493,497.

[30] Foreign Application Priority Data

May 11, 1965 [ZA] South Africa .......... 65/2502
Dec. 8, 1965 [ZA] South Africa .......... 65/6633

[51] Int. Cl.² .......... B01D 15/08; B01D 53/14
[52] U.S. Cl. .......... 210/65; 210/198 C; 55/386; 261/94; 261/112
[58] Field of Search .......... 55/386, 67; 210/198 C, 210/31 C, 65; 261/94–104, 112, 113

[56] References Cited

U.S. PATENT DOCUMENTS

| | | | |
|---|---|---|---|
| 3,079,134 | 2/1963 | Winn | 261/113 |
| 3,235,234 | 2/1966 | Beaudoin | 261/112 |
| 3,343,821 | 9/1967 | Winn et al. | 261/112 |
| 3,348,825 | 10/1967 | McIlvaine | 261/98 |
| 3,463,222 | 8/1969 | Grames | 261/112 |
| 3,475,012 | 10/1969 | Britton et al. | 261/112 |
| 3,687,818 | 8/1972 | Porter et al. | 261/101 |
| 3,796,657 | 3/1974 | Pretorius et al. | 261/94 |

Primary Examiner—Thomas G. Wyse
Attorney, Agent, or Firm—Millen & White

[57] ABSTRACT

In a process for separating miscible substances by mass transfer between two phases, at least one of which is a fluid phase (gas, vapor or liquid) and the other phase being a solid phase or a liquid phase (stationary or flowing in countercurrent with the aforesaid fluid phase, the mass transfer takes place and is substantially confined to the outside of the surface regions of the solid parts of porous material having the structure of an open pore foam, preferably substantially reticulated. This structure can be industrially reproduced in an idealized fashion in the form of interleading pores between which the solid parts are outlined in all three dimensions by concave shapes of spherical to near-spherical curvature corresponding to the outlines of densely packed phases.

Column packings for chromotography, distillation, countercurrent extraction and similar process. The advantages are low pressure drops combined with high flow rates (which in the case of chromotography are advantageously in the turbulent range), low theoretical plate heights.

18 Claims, 17 Drawing Figures

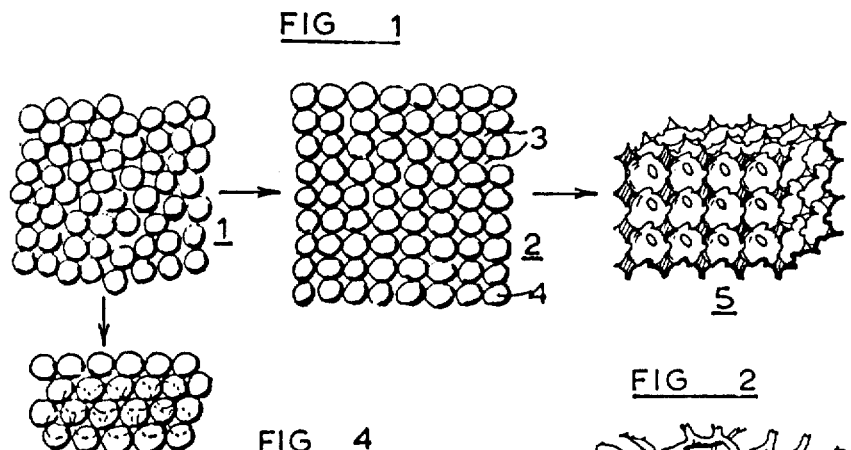
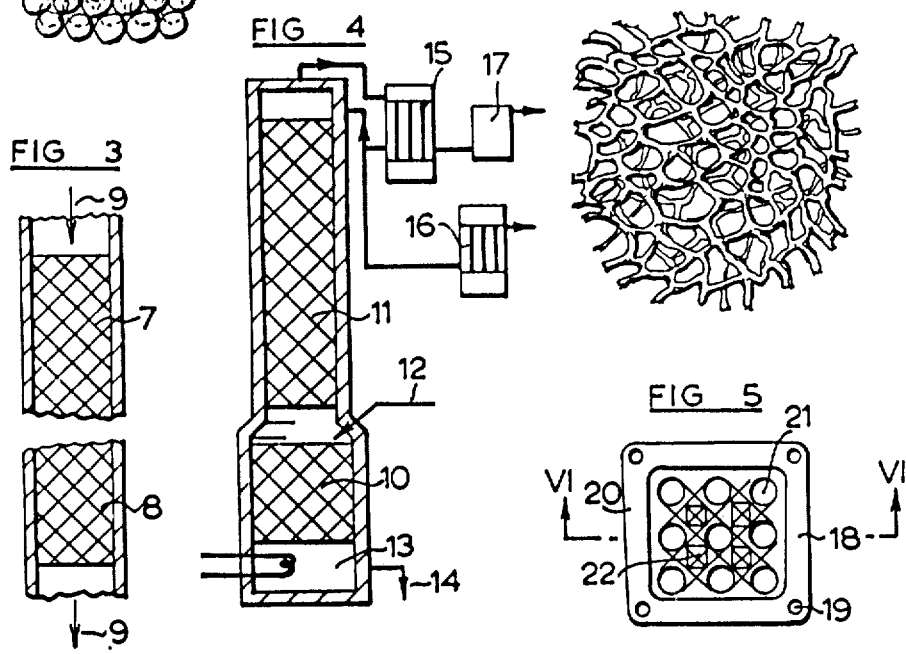
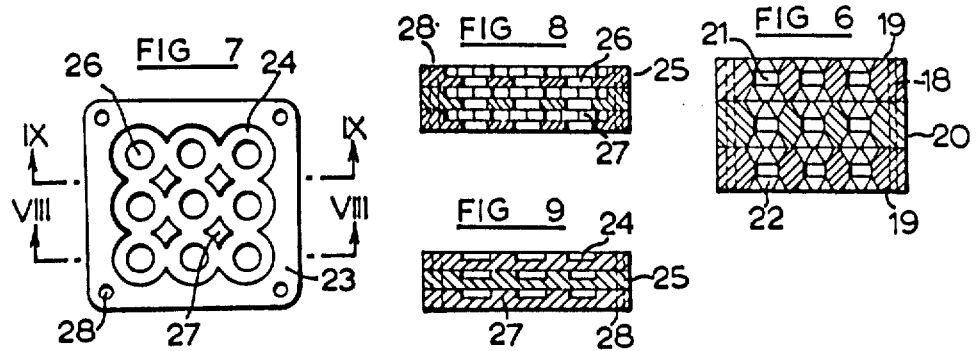

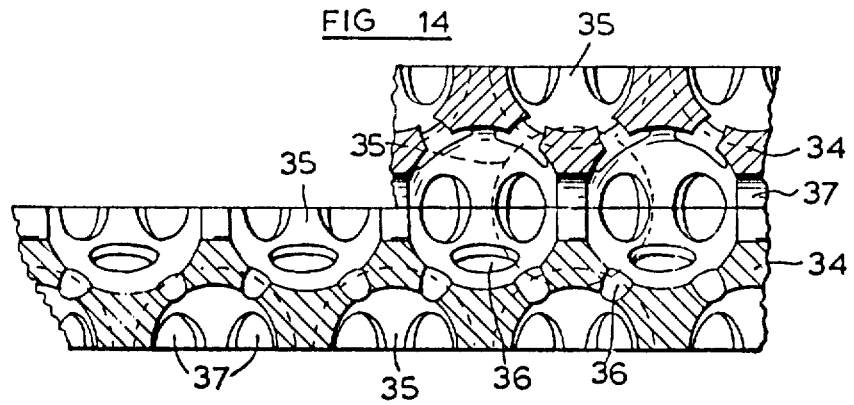
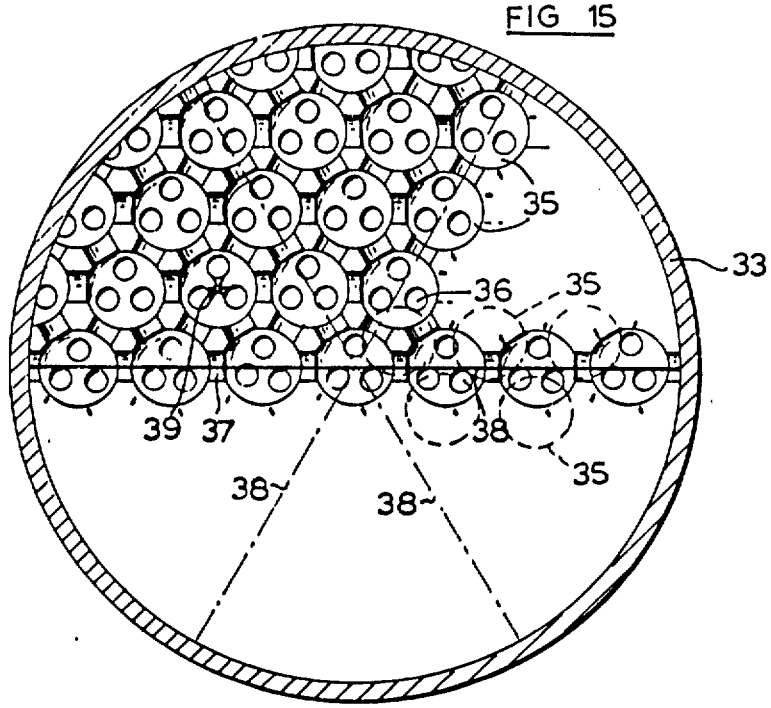
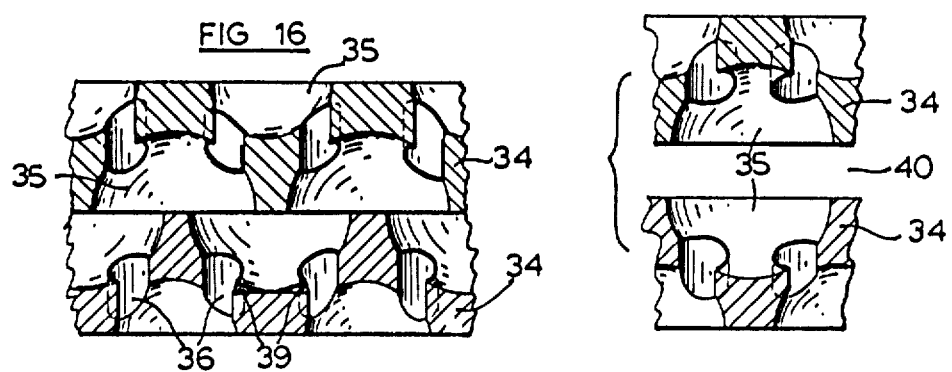

APPARATUS FOR DISTRIBUTION SEPARATION PROCESSES

BACKGROUND OF THE INVENTION

This is a continuation of Ser. No. 700,891, filed June 29, 1976 which is a continuation of Ser. No. 423,710 filed Dec. 11, 1973, now abandoned, which in turn is a continuation-in-part of Ser. No. 86,621, filed Nov. 3, 1970, now U.S. Pat. No. 3,796,657, which is a streamline continuation of Ser. No. 598,365, filed Dec. 1, 1966, abandoned, which in turn is a continuation-in-part application of Ser. No. 548,900 filed May 10, 1966, now U.S. Pat. No. 3,493,497.

The present invention relates to distribution separation processes involving mass transfer of miscible substances between two phases and apparatus therefor, more particularly for distribution processes in which the skeletal surfaces of packings serve as one of the phases between which distribution takes place or in which the packing provides a support or carrier surface for one of the phases.

Examples of processes to which the present invention may be applied are those in which one phase is stationary and the other, a fluid phase, is moving and those in which both phases are fluid phases (at least one being a liquid phase) and move relative to one another and to the said support or carrier surface, more particularly in countercurrent. Thus the invention is applicable to chromatography (batchwise and continuous), distillation (batchwise or continuous, including special forms such as vacuum distillation, steam distillation), adsorption (from gas or liquid), liquid/liquid or liquid/gas countercurrent extraction. In the context of chromatography, for example, the invention now teaches certain techniques which previously had not been considered suitable, although they had been used in somewhat comparable form, e.g. in distillation. As a result of this, the invention also extends to cases where the different processes listed above merge one into the other and where it may become artificial, for example to distinguish between continuous chromatography using a vaporous forwarding phase, and continuous steam distillation or between continuous countercurrent extraction and continuous chromatography.

According to one particular aspect the present invention relates to chromatography. In conventional chromatographic columns the separating efficiency is impaired by inhomogeneities resulting from uneven degrees of packing and variations in particle size, the latter having been almost unavoidable to date for reasons of economics, the former being very difficult to avoid completely for technical reasons and both factors being in part interrelated. Imperfections along the column walls resulting in channels differing from those in the packing interior are a most serious problem, virtually unavoidable even with the best compacted powder packings. Similar problems also arise in packed distillation or packed absorption columns. A main consequence of such imperfections is a pronounced, frequently irregular velocity profile (fingering) transverse to the direction of net flow, in turn leading to increased plate heights.

The effect of velocity profiles may be counteracted in chromatography by mixing of the forwarding (mobile) phase transverse to the direction of net flow (radial mixing in the case of ordinary columns). The comparative compactness of most conventional packings hampers such mixing both directly as well as indirectly by making more difficult the attainment of high flow velocities. In granular packings the porosity can be increased by looser packing which, however, results in undesirable mechanical instability.

It is an object of the invention to overcome or mitigate the aforesaid disadvantages.

Another object is the attainment of comparatively large and/or evenly accessible surface areas in the column combined with a comparatively high permeability and relatively low pressure drop.

The invention is furthermore intended to make available a very wide choice of different surfaces from which a person skilled in the art may select that type which in respect of inertness or other desired properties best meets his purpose and in such respect may be superior to other conventional columns for the same purpose.

The invention also provides for variability in respect of rigidity or resiliency or flexibility of the column material as may be required or desired for any particular application.

The invention provides for an almost unlimited variability in respect of pore size of the column and the void volume in accordance with certain embodiments may be as high as 97% of the total volume.

Certain embodiments provided for in accordance with the invention are of extraordinarily light bulk weight and low cost, both factors being of considerable importance in the construction of large scale apparatus.

Another advantage attainable where applicable with certain embodiments is the avoidance of preferential liquid accumulations, e.g. of chromatographic retarding phase or of liquid phase in distillation or extraction, in the nips between adjoining packing particles.

It is not essential that all of the above objects or potential advantages be realised simultaneously or to the same degree, since the emphasis may be shifted depending on requirements in each individual case.

The means in accordance with the invention may even serve as a support for the separating medium in dialysis, and the invention is quite generally applicable to techniques where it is desired to improve contact between two phases for the purpose of mass transfer of substances soluble or miscible in both phases.

It has been known before to employ open pore plastics foams, in particular polyurethane foams, and in particular those of reticulated configuration for the purpose of separating immiscible phases from one another, U.S. Pat. No. 3,171,820, describes the manufacture of such foams and mentions the use of such foams as filtering devices. U.S. Pat. No. 3,410,057 describes the use of such foams in gas/liquid apparatus for gas-liquid disentrainment. In accordance with the latter patent the vapour or gas rising from a bubble cup tray or similar device, e.g. in a distillation or gas scrubbing column and which carries with it entrained liquid droplets, is passed through a bed of randomly packed reticulated foam bodies. The object is for the gas or vapour to flow through the voids between the foam bodies, whilst the entrained liquid droplets are caught on the surface of the foam bodies (due to their wettability) and drawn into the foam interior due to surface tension effects. The foam bodies fill up with liquid like a sponge and the liquid drains downwards through the foam material under the influence of gravity, largely protected against the entraining forces of the gas or vapour. The intimate contacting of the gas and liquid phase with one another for the purposes of mass transfer takes place at the bubble cup devices for the like and not in the foam bodies where the two phases are substantially removed from one another, and follow different paths out of contact with one another.

U.S. Pat. No. 3,347,020 describes the use of such foams, e.g. polyurethane foam as a stationary phase in gas chromatography. In that case the foam is cut into pieces or ground up and packed into tubes with moderate pressure, whereby only part of the original porosity remains available. The pressure drop, although lower than for certain conventional backings, was therefore still appreciable. The main object in that case was to use the resin itself as the stationary phase, for which purpose the resin performs like a solvent of high viscosity. Because the mass transfer in that case is not confined to the skeletal surface regions of the foam, but the substances being separated are dissolved throughout the resin, the comparatively slow movement of molecules into and out of the resin becomes the controlling factor which limits the maximum flow velocity through the column to conventional linear velocities in the laminar range of flow.

In accordance with U.S. Pat. No. 3,357,158 it is known to carry out vapour or gas chromatography using as a packing micro-porous rosinous polymers having a plurality of interconnecting pores therein. However, these interconnecting micro-pores do not constitute the real flow passages for the forwarding phase. The flow passages proper are formed by the voids between the particles, and these are subject to the same characteristics as the flow passages in any other conventional packing composed of a bed of powder.

SUMMARY OF THE INVENTION

In accordance with the invention an apparatus for a distribution separation process is provided comprising a porous packing having three-dimensionally interleading voids for the throughflow of at least one phase bounded by surfaces exposing at least one other phase, said packing furthermore comprising the following features in combination:

(a) that solid portions thereof encompassing a plurality of said interleading voids are mechanically coherent;

(b) that in any one cross-section taken normal to the direction of net flow through the apparatus the void portions are interrupted by solid portions mechanically fixed relative to one another; and (c) that the porosity characteristics are essentially uniform across the entire packing transverse to the direction of net flow.

In the above definition "exposing at least one other phase" is intended to include the special case where the exposed surface of the packing itself serves as such phase (i.e. where the exposed surface has adsorptive or ion exchange or chelating properties, originally present or introduced by special treatment). However, in that case it is desirable that the said surface region or the material of the packing itself should be sufficiently impenetrable so that the mass transfer for all practical purposes remains wholly confined to the surface region. The expression also includes the case where a phase different from the packing is supported on the surface. "Supported" need not mean that such other phase is necessarily stationary relative to the packing since such meaning would exclude for example a distillation column in which the liquid phase will necessarily flow downwards over the surface of the packing in countercurrent with the vapours rising through the voids of the packing.

The invention also provides for a distribution separation process of the type in which one fluid phase flows relative to a second phase and a separation takes place by material distribution between the phases, comprising:

(a) maintaining said one phase on the surfaces of the voids of a porous packing confined in an enclosure and having essentially the features as defined further above;

(b) introducing into said enclosure a material to be separated;

(c) passing through the packing and enclosure said fluid phase whilst the material to be separated experiences distribution between the phases; and (d) withdrawing from said enclosure at least part of the material to be separated with a composition different from its composition prior to its introduction into said enclosure.

In accordance with a particularly preferred aspect of the invention there is provided apparatus for achieving mass transfer of mutually miscible substances between two fluid phases in intimate contact, in countercurrent with one another, comprising: a separation space containing a porous structure having essentially the texture of an open pore foam composed of interleading pores and skeletal surfaces outlining the pores, the pores serving as flow channels for one of said fluid phases and the skeletal surfaces serving as carrier surfaces for the other of said fluid phases, being a liquid phase, the porous structure in cross-section extending essentially continuously, uniformly and at least predominantly coherently across said entire space, said skeletal surfaces being the essential contact area between said phases for the mass transfer of the mutually miscible substances; means adapted for introducing the fluid phases in countercurrent with one another and for introducing said mutually miscible substances into this space; and outlet means adapted to withdraw from said fluid phases containing said mutually miscible substances.

"Mutually miscible" means "mutually miscible at least in the presence of a common solvent."

To a greater or lesser extent said porous structure may also extend substantially continuously and coherently not only across said space, but in the third dimension as well.

In a preferred embodiment said porous structure is assembled from a plurality of porous integral panels in which said texture repeatedly recurs in the two larger dimensions of each panel. Moreover, it preferably recurs at least twice over the thickness of the panel.

For use in apparatus as aforesaid there is also provided in accordance with the invention a packing body for providing in an apparatus packed with such bodies skeletal surfaces suitable as contact areas between two interacting phases, at least one of which is fluid, and flow channels between the skeletal surfaces for the said fluid phase, said body being in the form of a porous integral panel, whereof the faces are formed essentially by a plurality of depressions, the depressions of opposite panel faces closely adjoining one another, adjoining depressions of opposite panel faces being interleading.

The above is considered as of particular utility in the context of large-scale apparatus such as distillation apparatus (for continuous or batch-wise operation), gas liquid and liquid/liquid countercurrent extraction apparatus, adsorption apparatus and the like, although it can be scaled down to be applicable to chromatography as well.

Also, in accordance with the invention there is provided a distribution separation process of the type in which a fluid phase flows relative to a second phase through a space having defined outlines and a separation takes place by material distribution between the phases which are intimately contacted with one another along the outside and both are confined to the outside of the solid surfaces of three-dimensionally interleading pores of a porous material composed of said pores and solid parts between the pores, the fluid phase being guided through the pores along a flow pattern directed by said solid surfaces, characterised in that the solid parts between the pores are formed by integral structures outlined in all three dimensions thereof by concave shapes of spherical to near spherical curvature, constituting said solid surfaces and facing the pores. More particularly the said concave shapes which direct the flow pattern, are arranged around the said solid parts essentially in a geometrical pattern corresponding to the outlines of densely packed spheres, this being also the pattern in which in an ideal foam, the bubbles constituting the pore cavities, are arranged. In the densely packed state each sphere is surrounded by twelve equal spheres, the pattern being that of a dodecahedron.

In various preferred embodiments the fluid phase is a gaseous to vaporous phase conducted through the pores in countercurrent with the second phase which is a liquid phase, the liquid phase flowing along said solid surfaces.

In the above and various other embodiments of the process wherein the fluid phase is a gaseous to vaporous phase, the latter is preferably conducted with a flow velocity at which flow conditions are essentially turbulent.

Thus in accordance with a further preferred aspect of the invention there is provided a dromatographic separation process wherein a mixture to be separated is introduced into a space having defined outlines occupied by a porous material having pores through which a fluid forwarding phase is caused to flow in intimate contact with a retarding phase exposed on surfaces of the pores, whereby components of the mixture to be separated are distributed between the phases in different distribution ratios and become separated, comprising the improvement that the second phase is exposed to the fluid phase on the skeletal surfaces of the porous material as aforesaid, said skeletal surfaces constituting the outlines of interleading pores of the porous material which has essentially the texture of an open pore foam, the forwarding phase being conducted through said pores with a flow velocity at which flow conditions in the forwarding phase are essentially turbulent.

If in the aforesaid embodiment the forwarding phase is a gas or vapour, the linear flow velocity of the forwarding phase through the space is preferably in excess of 15 cm per second.

From the following more detailed description and explanation of the invention, largely by way of specific examples and in part with reference to the accompanying drawings various additional and/or preferred optional features as well as advantages of the invention will become apparent.

The following description of preferred embodiments should be read in conjunction with and in the context of what has been described in the aforegoing.

BRIEF DESCRIPTION OF THE DRAWINGS

In the drawings,

FIG. 1 illustrates diagrammatically different stages in the manufacture of a packing for a separating apparatus in accordance with the invention;

FIG. 2 represents a general view of the structure of yet another form of packing suitable for the invention;

FIGS. 3 and 4 represent diagrammatic sections through some typical examples of apparatus in accordance with the invention;

FIGS. 5 and 7 represent diagrammatic plan views of alternative packings, for apparatus in accordance with the invention.

FIGS. 6, 8 and 9 represent sections along lines VI—VI, VIII—VIII and IX—IX respectively in FIGS. 5 and 7;

FIG. 14 represents a vertical section through part of two panels in accordance with the invention assembled to form a packing structure similar to that illustrated with reference to FIG. 1;

FIG. 15 represents a plan view of panels similar to those illustrated in FIG. 14 installed as a packing in the column;

FIGS. 16 and 17 represent views similar to FIG. 14 of two panels similar to those shown in FIG. 14, but arranged in different relationship to one another.

DESCRIPTION OF PREFERRED EMBODIMENTS

Figure 10:
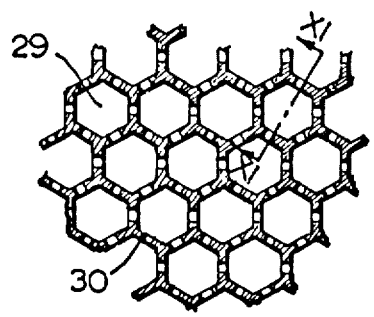
FIG. 10 represents a cross-section through a further embodiment of a packing.

Referring now to FIG. 1 a material consisting of substantially spherical particles or bodies is shown randomly packed. This condition normally lacks uniformity and closely approximates a conventional packing in a chromatographic column or in a packed distillation or adsorption column (e.g. glass beads). Provided the particles are solid and disregarding blind pores in packing materials such as kieselguhr, the void volume is at the most 40% of the total bulk volume, when as in the example shown the particles are of uniform size, e.g. obtained by screening. In practice, a considerable particle size range prevails normally in chromatography, resulting in a considerably reduced void volume percentage.

In practising the present invention a void volume of at least 45% is preferred, disregarding blind pores, and if possible more. Moreover, uniform porosity conditions, i.e. pore size and shape distribution and overall porosity must be assured at least across the entire packing transverse to the direction of net flow and preferably in the direction of net flow as well. Under randomly packed conditions the odds weigh heavily against such uniformity even in the packing interior and even more so in the vicinity of the confining walls.

Perhaps the best practical test for uniformity is actual separating performance, and whilst it may be difficult to lay down rigid limits, it will generally be true that a packing producing no more than 20%, preferably no more than 10% localised variations has very good uniformity by comparison with the prior art.

Therefore according to one embodiment, the material 1 is fluidized in a manner known as such, i.e. by blowing a fluidising medium e.g. air from underneath in an evenly distributed manner until the powder bed becomes turbulent and assumes the flow properties of a thin boiling porridge. The air flow is then reduced until the turbulence just ceases completely and the particles just rest in contact with one another in the uniform and well-defined metastable condition of loosest packing 2, in which the air flow just balances the tendency of the particles to fully settle to a more densely packed condition. The formation of the required uniform metastable state may be assisted by vibration. In this condition the void volume of the material is 48%, and in this condition the particles are bounded together. For example, the particles consist of or are coated with a sinterable material, e.g. glass or metal beads, wax, thermoplastic resin such as polyhydrocarbons, polyvinylchloride, fluorocarbon resins, polyamides, chlorinated polyethers, silicone resins, polyacrylates or uncured or partly cured reaction-curing resins, e.g. epoxy resin in the B-cure stage, solid at room temperature but still sinterable. Some polymerisation processes result in substantially globular particles from the outset. Such powders are then (if necessary) screened to produce a narrow particle size range.

Other materials may be transformed into spherical particles by casting the fused material through a screen (shot tower technique).

Sintering together of the particles to fix them uniformly in the expanded state of the material is achieved according to one embodiment by raising the temperature of the aerating medium as well as the temperature of the vessel in which aeration takes place.

The interstices 3 are now filled up with a reaction curing resin, e.g. an epoxy resin. After curing of this resin the originally particulate material 4 is dissolved or fused or volatilised and removed from the packing, leaving behind a porous body 5 having a void volume of 52%.

Substantially, a similar texture may be attained by expanding the product 2 with internal pressure until the spheres have been stretched and distorted to much the same shape and pattern as that illustrated by 5. Such internal pressure may conceivably be attained by filling the interstices 3 with a material expandible by heat or solvent action and subsequently removable e.g. by volatilisation, or solution.

It is also possible to employ beads 1 coated with a bonding agent which after the attainment of condition 2 is rendered tacky by heat or the temporary introduction of a solvent vapour or chemical reagent. In a similar manner solid polymethylmethacrylate particles may be bonded together by temporarily introducing into the air or other fluidizing medium a high proportion of chloroform.

For sintering it is also possible to apply heat dielectrically where the particles are non-conductors (as in the case of the substances just mentioned).

In the case of metallic particles amenable to induction heating, even where the cores only of individual particles comprise such metal, it is possible to employ induction heating for the purpose of sintering.

Some of the techniques for producing porous bodies from particulate materials are already known in different contexts and can be readily adapted for the purpose of the present invention with or without modification such as those mentioned in the aforegoing. For example sintered metal beads (bronze) are employed in the manufacture of filters, e.g. dl filters for motor vehicles. The manufacture of porous glass bodies by sintering is also a well established art and so is the sintering of plastic powders into porous bodies, e.g. battery spacers.

Where powders, e.g. certain plastic powders have a well defined melting temperature instead of passing through a plastic range, complications arising therefrom may in some cases be overcome by suitable compounding, e.g. the incorporation of fillers, in a manner well known in the art of plastics manufacture and processing.

Provided friction between the particles is extremely low and the particles are highly uniform and spherical another well defined completely uniform condition 6, namely that of closest packing is attainable. This material has a low void volume of only 26%. On the other hand if an aggregate of the particles in that condition is prepared in a matrix which is then solidified, the removal of the particles from the voids leaves behind a void volume of 74% very favourable for the purposes of the invention.

This condition is indeed a perfect replica of an ideal open pore foam whch can also be reproduced in a variety of other manners for the purposes of the present invention. The void volume and degree of communication between the spherical voids can be increased further in a variety of manners, e.g. by increasing the areas of contact between the spherical particles, by more intensive sintering or the use of a bonding substance prior to casting the matrix.

If the same technique is applied to an aggregate having the particles arranged at random in accordance with 1, the void volume of the matrix after removal of the particles will be approximately 60%.

Again this void volume can be increased somewhat as well as the degree of communication between the spherical voids in the same manner as described in the previous paragraph.

If the original particles have been chosen in a reasonably narrow size range and have been reasonably evenly packed, the eventual porous coherent matrix may satisfy the practical requirements of uniform porosity for the purposes of the invention, even though the randomly packed powder itself did not. This is so because in the porous matrix the pore shapes and dimensions are positively controlled by the corresponding shape and sizes of the particles substantially removed.

In the various embodiments of this type, the matrix may be organic or inorganic. It may be employed in the form of a liquid or semi-liquid substance which subsequently hardens by chemical reaction, e.g. a reaction curing resin such as polyeter or epoxy resin or an inorganic cement such as Sorrel cement, or for some purposes even Portland cement or plaster of Paris. It could conceivably be a colloidal system such as a clay slurry which subsequently hardens by loss of water and which may, when so required, even be fired eventually with or without glazing.

Other matrix materials, e.g. fusible resins, waxes, low-melting metals or glasses may be employed in a molten condition and caused to solidify by cooling.

The particulate material for the aggregate must be chosen depending on the matrix so that the subsequent removal of the particles does not remove or damage the matrix as well, as will be readily understood. Suitable substances to be removed by melting are beads of waxes, resins or metals melting lower than the matrix. Beads of metal may also be leached out with acids. Beads of waxes, bituminous or other organic substances may be dissolved out with the appropriate organic solvents. Beads of sulphur can be melted out or dissolved in carbon di-sulphide, pellets, or beads of various salts, gelatine, starch or the like may be leached out with water. Most organic and some inorganic substances can also be removed with heat to cause their volatilisation, in some cases with decomposition.

The term "packing" as used in this specification is to be understood rather in the colloquial sense in which the term is generally used in the art, i.e. a material constituting the solid filling of a column or like apparatus interspersed by voids or pores. The term does not in any way imply that the material has been forcibly packed or rammed into the apparatus.

The term "pores" in this context is not to be given a narrow interpretation but is rather to be understood as a relative term with reference to the cross-section of a column or like apparatus.

The voids may take the form of pores of a variety of shapes and proportions. According to one extreme and preferred embodiment for many purposes the voids or pores are by far the predominating feature of the column, the solid part constituting but a skeletal structure occupying as little as 3%, say between 2 and 5% of the entire column volume. Thus according to a particularly advantageous embodiment the column packing is essentially a foam with an open pore structure, more particularly a reticulated foam.

Such foam may be produced from any material suitable to form a packing and capable of being transformed into a foam, be it organic or inorganic. Examples of foamable inorganic materials are glass, slag, calcareous binders, including portland and related cement compositions, plaster of Paris.

Examples of suitable organic compositions are in particular to be found in great variety amongst various classes of synthetic resins. The ideal foam structure is shown in FIG. 2, which may be attained with various commercially available foam plastics. The texture is for example known in various flexible polyurethane foams, particularly of the polyether type. By techniques known as such the pore dimensions may be varied within wide limits. Silicone and other open-pore foams have more or less the same structure. The method of producing the foam structure will depend on the nature of the foamable material.

A foamable material may for example be foamed by being whipped up with gas or air to form an open pore foam from the very outset which is then caused to solidify, e.g. by chemical reaction, in particular polymerisation or polycondensation, or by cooling (freezing).

An aqueous foam may for example be produced with the aid of suitable foaming agents (surfactants), e.g. sodium alkyl aryl sulphonates, sodium lauryl sulphonate and the like, and caused to solidify by the gelling in said aqueous system of a synthetic resin. The resin may for example be urea formaldehyde resin, the gelling of which may be brought about with the aid of an acid catalyst, preferably phosphoric or oxalic acid. Urea formaldehyde foams and processes for their production are known as such and require no further discussion. The rigidity of urea-formaldehyde foams may be improved if desired by various additives. In somewhat similar manner known per se it is possible to produce melamine formaldehyde and phenol or resorcinol formaldehyde foams. The above foams may be produced with a very even pore distribution.

In some cases plastic or other foams (both open pore and closed pore) may be produced by the release of gas as a result of chemical reaction of the ingredients of the foam forming material. Typical examples of suitable foams thus producible are rigid and resilient polyurethanes, both of the ether and the ester type.

Polyurethanes which from the outset have the desired open pore structure may for example be produced by the reaction of diisocyanates and a polyol in the presence of a blowing agent, e.g. $CO_2$ liberated by the reaction of an excess of diisocyanate with water, preferably in the presence of a surfactant, e.g. a silicone surfactant and a catalyst, e.g. tin catalyst.

Another foam having a suitable open pore structure is polyvinylchloride foam produced by chemical blowing, in particular by the low density vinyl extrusion process.

So-called reaction type phenolic foam can also be produced with a suitable open cell structure.

Particularly suitable for many purposes because of their chemical and thermal stability are foamed silicones, e.g. silicone rubber foams, which similarly to some other aforementioned foams can be produced quite successfully by in situ foaming.

In some cases, however, the foam texture is initially less perfect than that shown in FIG. 2, in particular by the presence of some lamellae between the skeletal struts of the foam. In some cases it may be possible to remove the lamellae by mechanical bursting, but the preferred method of removal is by chemical leaching or solvent action. This procedure may also be applied to certain foamed slags or foamed glasses, in particular soft glasses, e.g. lead glass, where hot strong alkali, e.g. 10 N KOH at 95° C., say for 50 hours is found effective. Thermal treatment may be resorted to in some cases. In the case of polyurethane foams ester type solvents may be employed. Suitable solvents for polyvinylhchloride and epoxy resins are of the ketone type, e.g. methylethyl ketone.

Considerable variation, depending on the intended use of the apparatus is possible with regard also to average pore size. In FIG. 3, for example, the packing 7 indicated diagrammatically by cross-hatching andd which could be any of the aforegoing is enclosed in a tube 8 to form an adsorption column or a chromatographic column, the movement of the mobile phase, either gas or liquid, being indicated by arrows 9. Because of the characteristics of the packing there is no change in average column density right to the interface between the walls 8 and the packing 7. To reduce any wall effect even further the packing material is preferably connected with, e.g. integral with or bonded to the walls of the column. Alternatively there is such a close fit that no or very little non-uniformity or discontinuity arises at the interface between column wall and packing. For example, where the packing is resilient, a close fit may be realised comparatively easily.

The packing may be bonded to the column walls with an adhesive inert to the substances employed in the separation, e.g. an epoxy resin or polyvinyl acetate adhesive.

Polyurethane foam precut to a cylindrical shape was successfully bonded to the inside of polymethylmethacrylate tubing by introducing the loosely fitting foam into the tubing and then just moistening the foam with chloroform. This caused the foam to swell against the inside of the tube and simultaneously to bond the foam to the tube by the solvent action of the chloroform on the tube material.

Such plastic foams as polyurethane may be cut into the required shape with hot wire.

The porous packing material may be cut up into strips and sandwiched between two sheet materials with impervious strips separating adjoining porous strips from one another and the extremities of the strips being joined to one another through pipe bends of comparatively small diameter to form a column having a total effective length equal to the sum total of the individual strip lengths, e.g. suitable for gas or liquid chromatography.

Many materials may also be foamed in situ inside the column walls when bonding of the packing to the walls will usually result. However, this technique is not recommended unless a foaming material and technique is adopted which ensures the formation of an even foam texture throughout the column cross-section.

The column walls 8 need not necessarily be rigid. Resilient forms of packing e.g. resilient polyurethane, P.V.C. or silicone rubber may be supplied incorporated in a flexible tube material, e.g. plastic tubing, suitable for forming a column wall, and the user will simply cut off the length of column required for his particular purpose and connect such length to a suitably adapted column inlet (head) and outlet means.

The foam or like packing may, for example, be produced in situ or injected into a preformed plastic or other tube, which for many purposes may be quite thin-walled, e.g. of the order of a few hundreds of a millimeter, and for other purposes may be quite strong, say several millimeters thick.

The skin, i.e. the column wall may in some cases also be applied to the pre-formed packing material or the packing material and column wall may be manufactured simultaneously, e.g. by simultaneous concentrical extrusion.

Suitable skin materials may (depending on the purpose of the column) be e.g. polyethylene, polyvinylchloride, polyamides, polyacetals, polyurethane and various natural or synthetic elastomers. In other cases the skin may consist of and be integral with the foam material.

Tubing of thermally shrinking plastics may be applied to the outside of preformed packing material and shrunk firmly into contact with the packing by heating.

The features of the invention are useful for chromatography on any scale, from microanalytical up to large-scale preparative work.

In accordance with a preferred embodiment the features of the invention are applied to large-scale columns, such columns having diameter of at least 10 cm, preferably at least 30 cm, more particularly at least 1 m. Such column diameters cannot be employed successfully with conventional chromatographic packings without excessive losses of separating efficiencies. In chromatographic columns it is preferred for the average cross-sectional area of the individual pore to be no more than 1%, preferably no more than 0.1%, more particularly less than 0.01% of the column cross-sectional area. According to some embodiments the pores may be of microscopic dimensions regardless of the cross-sectional area of the columns.

On the other hand, particularly in the case of columns of large diameter, e.g. of 30 cm or more, the pores may have a diameter of up to 1 cm or more with a consequential reduction in pressure drop through the column when in operation at the expense of some capacity. It is interesting to note that with some packings having the texture in accordance with FIG. 2, plate heights have been measured of less than the average pore diameter.

The exposed surface of the packing material may itself serve as a stationary phase or be surface treated e.g. chemically, to become a stationary phase or serve as a support for a stationary phase material subsequently applied. In the latter case the stationary phase may take the form of a solid coating, e.g. a layer of colloidal carbon, a precipitate of active alumina, or a gelatinous film, more particularly a deposit of silica gel or synthetic resin, e.g. an ion exchange resin. In particular, however, the packing may serve as a support for various liquids known in the art for that purpose, both polar and nonpolar. If necessary the packing may be subjected to treatment, e.g. with monochloro trimethyl silane or dichloro dimethyl silane to reduce the polarity of the packing surface in a manner known per se. The packing is then impregnated with any suitable retarding phase, e.g. in manners well known in the art.

Where the column packing consists e.g. of polyethylene or polyvinylchloride it is possible to sulphonate the exposed surfaces of the pores to impart ion exchange properties to the packing. In other cases the column is first impregnated e.g. with a silane, prior to such sulphonation.

Because of the low pressure drop through the packing materials herein described, particularly those of high volume, it becomes feasible to carry out chromatographic separations, concentrations or purifications on a large scale inside pipelines, whilst materials are conveyed through such pipelines from one locality to some other remote locality.

A preferred manner of carrying out chromatographic separations in pipelines is described in our said U.S. Pat. No. 3,493,497, the pressure drop through the material of given pore characteristics is either available or can readily be determined by routine experiments. The pressure drop which can be tolerated for any given pipeline, and therefore the choice of packing material from the various embodiments herein described, is largely a matter of economics as will be readily understood by persons skilled in the art.

The pore structures lend themselves excellently to chromatography carried out at high speed, e.g. up to several orders of magnitude higher than hitherto customary. It is an inherent characteristic of the packings herein described that the velocity profiles in chromatography are remarkably flat and that "fingering" is hardly if even observable. The just mentioned unusually high operating speeds can be employed to attain increased throughput and/or separating speed. They can be employed in addition to flatten the velocity profile even further and in particular to eliminate any wall effects. By raising the flow velocity above a predetermined velocity (best expressed as a Reynolds number) there will be achieved a fairly sudden improvement of transverse dispersion because of the development of turbulent eddies behind the solid obstructions (plateau regions) of the packing. Where the forwarding phase is a liquid the preferred linear flow rate is at least 0.2, preferably 0.3 cm/sec. Where the forwarding phase is a gas and subject to the nature of the retarding phase permitting such high speeds, the preferred linear flow rate is above 15 cm/sec., preferably above 20 cm/sec, more particularly at least 30 cm/sec.

The extraordinary characteristics of the packings in respect of mechanical coherence and uniform porosity permit radical departures from conventional column design. Thus it becomes possible, when convenient to deviate from the circular column cross-section at present generally employed.

When the apparatus in accordance with FIG. 3 is employed as an adsorption column, its high permeability is a particular advantage. The packing may be impregnated with a liquid or solid adsorbent or a chelating agent.

For larger size industrial type apparatus it is preferred to employ either the packings described with reference to FIG. 2 which may be introduced into the column in the form of suitably dimensioned blocks or slabs, and which are then assembled in the column to form a continuous porous structure, or one of the simulated foam packings, e.g. as described further below with reference to FIGS. 10 to 17. For gas scrubbing purposes it is possible in a conventional manner to apply to the top of the column a scrubbing liquid, the packing having good wetting properties for such liquid, and letting this liquid run down the column as a film covering the skeletal surfaces of the packing in countercurrent with the gas or vapour introduced into the bottom of the column and flowing to the top through the voids outlined by the skeletal surfaces of the packing.

In FIG. 4 the application of the invention to an otherwise conventional continuous distillation apparatus is illustrated, but it will be readily understood that the invention may be applied similarly to laboratory size and batch distillation apparatus. The apparatus shown comprises two column sections 10 and 11, each packed with a packing as described above, indicated diagrammatically by cross-hatching, preferably having the foam texture in accordance with FIG. 2, or that of the matrix described with reference to FIG. 1, introduced into the column e.g. in the form of blocks or slabs. For larger columns in particular it is preferred to employ one of the packings in accordance with FIGS. 10 to 17. The material to be separated is introduced in vapour form at 12. The high boiling fraction collects in the heated sump 13 from which some material is continuously withdrawn at 14. The low boiling fraction is condensed in condenser 15, part of the condensate being returned to the column head as reflux, the remainder being withdrawn through a cooler 16, light vapours being condensed at 17.

In the case of columns for distillation comparatively coarse textures, i.e. uninterrupted voids of comparatively large cross-section are advantageous to minimise flooding of the column. In the case of large scale distillation plant the voids may have diameters of several centimeters. Again, because of the uniform porosity and the decreased wall effects a column cross-section other than circular may be employed if convenient. For distillation as well it is possible to treat the surfaces of the packing so as to render them more polar or less polar thereby to modify the wetting characteristics.

The various packings herein described may also be coated with any suitable coating material to render the packing more inert to the materials with which it is to come into contact in the distillation or chromatographic or other separating process. For example, some of the foams herein described were successfully coated with waterglass or with a commercial brand of floor sealing composition.

It will be appreciated that an apparatus substantially having the configuration shown in FIG. 4, with suitable adaptations as to dimensions and the omission of heating and condensing means, could also be employed for countercurrent extraction of substances introduced at 12, either extraction in a gas liquid system or in a liquid-liquid system. For that purpose one liquid phase having good wetting properties for the packing employed would be applied to the top of the column 11 and would run down to be withdrawn at 14, forming a continuous flowing film on the skeletal surfaces of the packing. The second phase, being a gas or liquid lighter than the liquid applied to the top of the column and substantially immiscible with that liquid, and having poor wetting properties as far as the packing is concerned, would be introduced at 13 and rise to the top, there to be withdrawn. The relative feed rates of the two fluid phases introduced to the top and bottom of the column respectively, can be so adjusted that, in view of the different partition ratios of the various components of the mixture introduced at 12, a particular component or components will travel down the column and will thus be withdrawn at 14 as one fraction, whilst another component or components, having the greater relative affinity for the upwardly moving phase, will travel upward through column 11 to be withdrawn as another fraction at the top of the column. This form of countercurrent extraction then becomes an embodiment of a continuous chromatographic separation process.

Greater versatility as regards the material to be used for the packings in accordance with the invention, the sizes of the pores and their precise geometrical arrangement and manufacturing convenience is afforded by a variety of methods to reproduce or simulate these textures in industrial manufacture.

Referring to FIGS. 5 and 6, a large number of discs 18 are provided, stacked and bolted together by bolts in positions 19. The discs, manufactured by moulding, e.g. injection moulding of plastics or rubber or by pressing a malleable material, e.g. metal may have any desired shape in plan view, the square shape shown being just one of many possibilities. It will also be appreciated that in practice the number of pores distributed over a given cross-section will normally be very much larger than is shown in the diagrammatic views of FIGS. 5 and 6. On both faces each disc carries peripheral raised rims 20 which in the assembly combine to form a column wall. The entire area of each disc surrounded by the rims is recessed on both sides of the disc with the exception of raised pyramidal formations 22, a pattern of holes 21 passing right through the recessed portions and the pyramidal formations 22 being present everywhere between the holes and rising to the same level as the rims 20. The result is once again a complete three dimensional regular network of pores and intervening struts. If desired the discs may be sintered or bonded together.

It will be seen that there are no wedge-shaped areas of contact as occur with randomly packed conventional packing bodies, nor is the regular pattern and uniformity of the pore distribution the result of laborious individual accurate positioning of small packing bodies. The desired skeletal structure is present in the porous integral panels in which the desired texture repeatedly recurs. For some applications the accurate alignment of the cells 23 as shown in FIG. 6, may be undesirable. This may be avoided by slightly modifying the pattern of the individual panels such that the cells in successive layer of the stack become offset relative to one another. Also for the sake of simplicity, the outlines of the cells in FIG. 6 have been shown partly angular, it is of course possible to provide a closer simulation of a true foam structure, more particularly a reticulated foam structure by rounding off any of the corners shown in the drawings. In this manner also the ratio of void to solid in the total volume may be increased at will.

Referring to FIGS. 7 to 9 discs 23 of metal, e.g. copper have been etched from both sides by a photographic etching process, the technique being for example similar to that employed in the manufacture of "printed circuits". From the one side overlapping circular depressions have been etched into the metal, a continuous rim 25 having been left standing. From the other side holes 26 of a diameter smaller than that of the depressions 24 have been etched through to the centre of each depression 24. Between the depressions 26 raised portions 27 are left standing. The discs are assembled and bolted together with bolts in positions 28 to form a column similar to that in accordance with FIGS. 5 and 6.

As in the case of the embodiment in accordance with FIGS. 5 and 6, a closer simulation of a true reticulated foam texture may be achieved by a more rounded-off pattern of etching as is apparent from the diagrammatic cross-sections in FIGS. 8 and 9, a more complete etching away of the solid portions to increase the void volume and a staggered arrangement of the voids in successive panels rather than the complete alignment as apparent from FIGS. 8 and 9.

Figure 11:
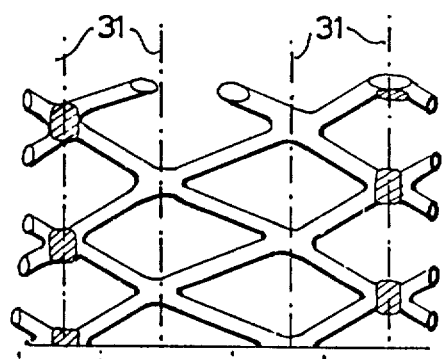
FIG. 11 represents a section along line XI—XI on an enlarged scale of a particular modification of the embodiment shown in FIG. 10.

Yet another possibility is shown in FIG. 10. Here a material of honeycomb-like cross-section has been extruded from plastics or metal to result in a bundle of capillaries 29. The walls between adjoining capillaries have been pierced at 30 to achieve complete three dimensional communication. As a further modification the piercing may be in the form of slots which are subsequently stretched open with simultaneous twisting deformation of the capillary walls in a manner known per se from the manufacture of expanded metal. This will then result in the kind of configuration illustrated on a larger scale in FIG. 11 where the corners of the hexagonal honeycomb cells are represented by broken lines 31. The structure of FIGS. 10 and 11 can be incorporated in a column, e.g. a distillation column either with the axes of the honeycomb parallel to the axis of the column or transverse thereto. If the honeycomb axes are parallel to the column axis, it is preferred for the structure to be employed in the form of panels stacked one on top of the other such that the honeycombs of successive panels are offset one against the other as illustrated in FIG. 11 where the corners of one of the honeycombs of an adjoining panel are indicated by broken lines 32.

It will be appreciated that the honeycomb structure of FIG. 10 need not necessarily be extruded. It could also be assembled from perforated, slotted or slotted and expanded sheets bent according to a meandering pattern, successive such layers being connected together by bonding, welding or any other suitable manner either with intermediate connecting webs if a hexagonal honeycomb pattern is desired, or directly (when the cell cross-section would be square or rhombic).

Figure 12:
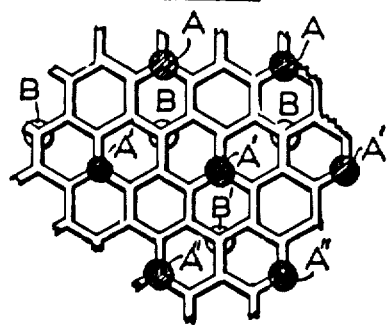
FIG. 12 represents a view similar to FIG. 10 of a different embodiment of the type of packing shown in FIG. 10.
Figure 13:
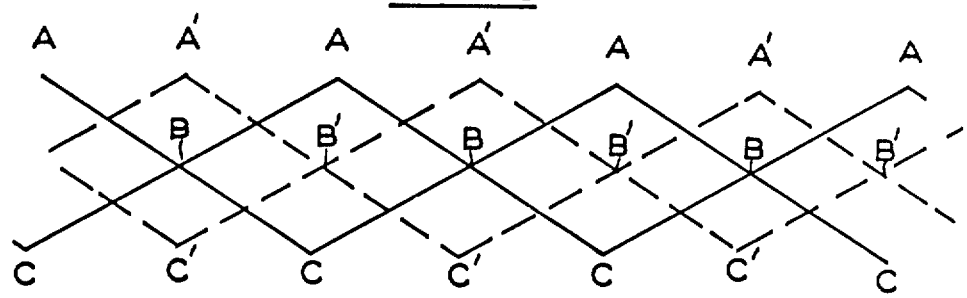
FIG. 13 represents a diagrammatic side elevation of the structure in accordance with FIG. 12.

The concept of FIG. 10 can also be modified as shown in FIGS. 12 and 13.

In accordance with FIG. 12 the structure according to FIG. 10 is divided into comparatively thin wavers stacked on top of one another and interconnected on the isolated points, the connecting points between successive wavers following a staggered pattern in plan view. Thus in FIG. 12 the waver (not shown) overlying the particular waver shown in the drawing would be connected at ponts A, A' and A". The next lower waver is connected on at points B and B'. These connections may be brought about by heat welding or bonding, soldering or any other suitable manner of mechanical connection. Traction is then applied to the completed stack of wavers in the directions parallel to the axes of the hexagons, resulting in an expanded structure which in side elevation follows the pattern diagrammatically shown in FIG. 13. Panels of such configuration may then be stacked in a column, either directly one on top of the other, or with spaces inbetween to constitute a column packing of high void volume and suitable for various processes contemplated by the invention.

Again it will be appreciated that the principle illustrated and described with reference to FIGS. 12 and 13, is not limited to wavers having a hexagonal honeycomb pattern. The grid material of the webs of FIG. 12 may also be replaced by other grid materials, e.g. wire mesh, alternatingly spot connected face to face at staggered localities and then stretched apart to form a three-dimensionally expanded structure. Such expanded structure may subsequently be dipped into suitable coating substances, either for protection or to increase the thickness and surface area of the struts.

The use of an expanded metal type of structure here described, differs substantially from conventional column plates of the sieve tray type in which the flow of gas or vapour from below, is so regulated that an appreciable thickness of liquid is maintained on the tray through which the gas bubbles.

Referring now to FIG. 14, the configuration of the matrix in accordance with item 6 of FIG. 1, and which constitutes the ideal configuration of an open-pore foam, may be reproduced industrially in a very convenient manner. The column packing (which in FIG. 15 is shown in plan view, the column wall being represented by 33) is assembled from a plurality of porous integral panels 34 of which two are shown in FIG. 14, in each of which the desired foam texture repeatedly recurs in the two larger dimensions of each panel. This texture is provided in that the faces of each panel are formed essentially by a plurality of depressions 35 (of which in FIG. 15 only some are shown). In compliance with a true idealised foam these depressions 35 are hemispherical, although the hemispherical shape could be modified somewhat to produce special flow effects. Adjoining depressions of opposite panel faces are rendered interleading by apertures 36, (each hemisphere being in communication with three hemispheres on the opposite side of the panel). In addition the adjoining depressions of the same panel face are also rendered interleading by the passages 37. In accordance with FIG. 14 the panels 34 are so stacked on top of one another so that the hemispherical depressions of adjoining panels are in matched relationship to form complete spheres. It will be appreciated that in the course of the manufacture, the sizes of the passages 36 and 37 relative to the sizes of the hemispherical depressions can be varied virtually at will to produce the desired column characteristics. In a typical distillation column of say, 40 cm diameter, the hemispheres may have a diameter of say between 2 and 3 cm. In a larger column of say 1 to 2 meter diameter, these hemispheres may for example, be between 3 and 7 cm in diameter, although it may be preferred even in those cases to employ smaller pore sizes to reduce the theoretical plate height of the column.

In FIG. 14 the panels are stacked in immediate contact one on top of the other.

In accordance with FIG. 15, the individual panels are hemicircular in plan view, two adjoining panels covering the entire column cross-section. The panels of successive layers, the outlines of which are indicated by lines 38, are off-set by 60° so that the joints in successive layers of panels do not coincide, and so that a single configuration of panel will nevertheless yield the geometrical pattern as illustrated in FIG. 14. Larger column cross-sections may be covered e.g. by a plurality of triangular panels, suitably assembled.

For special flow effects the different relative positioning of the panels in accordance with FIG. 16, may be adopted where the panels 34 are so superimposed that the adjoining hemispheres of successive panels are off-set against one another in staggered relationship. In that case the passages 37 of FIG. 14 can be dispensed with.

In FIG. 14 it is assumed that the connecting apertures 36 are arranged radially in respect of the centres of the respective hemispheres. Since the panels are to be manufactured by moulding or casting from plastics, metals, cementitious or ceramic materials, the aforesaid configuration of holes is somewhat difficult to reproduce by certain available methods. A simplified pattern, satisfactory in many cases and more easily manufactured, is illustrated in FIGS. 15 and 16 where the holes 36 have their axes normal to the face of each panel.

If it is desired to reduce the holdup of the column, it is possible to provide grooves 39 between the holes of the depressions 35 to facilitate drainage of liquid.

Referring now to FIG. 17, the same panels as in FIG. 16 are employed. However, in this case the panels are stacked with a gap 40 between successive panels. In that case again there is transverse communication between the hemispheres 35 even without passages 37 as shown in FIG. 14.

When employed in a countercurrent process, the flow pattern in accordance with FIGS. 16 and 17 differs from that in accordance with FIG. 14. In accordance with FIG. 14 the liquid film flowing over the skeletal surfaces of the pores can flow continuously from one panel to the next. In accordance with FIGS. 16 and 17 the said liquid film is ruptured in the form of drops falling from one panel onto the next where the liquid film is then remade. The type of flow pattern most favourable for any given set of circumstances, will have to be decided upon from case to case, and the panels here described permit adaptation to either set of conditions.

It will be understood that the hemispheres in the panels according to FIGS. 14 to 17 are arranged in a pattern essentially corresponding to the geometrical pattern of the peripheries of densely packed spheres.

It will further be appreciated that the use of the panels according to FIGS. 14 to 17, or of the packings described with reference to FIG. 1, i.e. a packing material having an ideal foam configuration, results in a distribution separation process of the type herein discussed in which a fluid phase flows relative to a second phase through a space having defined outlines and wherein separation takes place by a material distribution between the phases which are intimately contacted with one another along the outside and both are confined to the outside of the solid surfaces of three-dimensionally interleading pores of a porous material composed of said pores and solid parts between the pores, the fluid phase being guided through the pores along a flow pattern directed by said solid surfaces, characterised in that the solid parts between the pores are formed by integral structures outlined in all three dimensions thereof by concave shapes of spherical to near spheric curvature constituting said solid surfaces and facing the pores.

EXAMPLE 1

A polyurethane column is prepared, foam texture as in FIG. 2, void volume 97%, 30 pores per cm, column length 187 cm, diameter 0.25 cm. The foam is coated with silicone oil introduced as a 10% v/v solution in petroleum ether, the latter being subsequently evaporated off. A sample of a mixture of normal paraffins from $C_4$ to $C_8$ is introduced (2.5 microliters) and eluted with hydrogen at a linear flow velocity of 10 cm/sec. The chromatogram is recorded in conventional manner, the first peak being due to butane, followed by pentane, hexane, heptane and octane. The pressure drop was only between 1 and 1.5 atm.

EXAMPLE 2

The same column is tested for plate heights at different flow velocities. With liquid eluents full radial dispersion is apparent by the attainment of a minimum plate height of 1 mm at 0.3 cm/sec.

With a gas as eluent the plate height at 15 cm/sec. is 0.5 mm, and drops to 0.2 mm at 30 cm/sec. which from the slope of the curve seems to be near the optimum. Another similar packing with 40 holes per cm produces a plate height of 0.1 mm at 30 cm/sec.

EXAMPLE 3

Detector probes are inserted in different packings of columns of 5 cm diameter. In conventional packings fingering is clearly discernable and there is a pronounced wall effect. With a packing having the same characteristics as in the previous example no fingering is observable at all and the wall effect is much less pronounced.

EXAMPLE 4

A silicone rubber foam column is impregnated with medicinal paraffin. The void volume is 85% and there are 20 pores per cm. 70% aqueous acetone is saturated with medicinal paraffin to serve as a mobile phase. A mixture of palmitic and stearic acids is dissolved in a small volume of mobile phase and allowed to seep into the column, whereafter elution proceeds with more 70% aqueous acetone. The column temperature is maintained constant at 30° C. by water jacketting. A complete separation of palmitic from stearic acid is attained at a linear flow rate of 0.3 cm/sec. 1 = 30 cm.

EXAMPLE 5

A column as described with reference to any one of FIGS. 5 to 9 is coated internally with a highly absorbtive layer of carbon black as follows:

The column is filled with a dispersion in a highly volatile liquid of colloidal carbon. Such dispersions are commercially available. The volatile liquid is carefully evaporated off and the coating of colloidal carbon is left behind. The thickness of the carbon coating can be controlled as desired by adjusting the concentration of the dispersion.

The thus prepared column can be used inter alia for the separation of oxygen from nitrogen gas using hydrogen gas or helium gas as a mobile phase. The conditions under which the separation is carried out are known as such from chromatography.

The active carbon layer may also be partly deactivated in a manner known per se by treatment with squalene whereafter the column is suitable for the separation of propane from butane and similar separation problems under conditions in other respects known per se.

EXAMPLE 6

Comparative experiments were carried out on a jacketted distillation column, inner diameter 50 cm, length 90 cm. The following packings were compared:

(a) Podbielniak heligrid;

(b) randomly packed porcelain Raschig rings 6×6 mm;

(c) polyurethane foam as in FIG. 2, void volume 97%, pore size approximately 5 mm.

Plate length measurements were carried out with the testing mixture n-heptane-methylcyclohexane. The following set of measurements was taken:

| Packing | a | b | c |
| --- | --- | --- | --- |
| throughput ml/hr | 4000 | 5000 | 5000 |
| holdup (ml) | 160 | 290 | 120 |
| pressure drop (mm Hg) | 5 | 23 | 5 |
| plate height (cm) | 1.3 | 12 | 1.1 |

In addition the maximum throughput before flooding was determined as follows:

(a) 6000 ml/hr
(b) 5200 ml/hr
(c) 6000 ml/hr

The results show that packing (c) is much superior to packing (b) and even compares favourably with packing (a) which latter is very expensive.

EXAMPLE 7

An experimental distillation column (20 cm diameter) is packed with berl saddles and the same column is subsequently packed with the packing in accordance with FIGS. 14 and 15, yielding substantially the same pore diameter (10 mm). Alcohol water is used as the test liquid. On average the separating efficiency in terms of theoretical plate height for different test mixtures and at different throughput rates, is between 2 and 4 times as high as that of the berl saddle column. (In other words, the column height can be reduced accordingly to achieve the same degree of separation). Regardless of the test liquid employed (different starting concentrations of alcohol) the column in accordance with the invention also permitted consistently higher throughputs before flooding occurred. The best theoretical plate heights are attained just before flooding, i.e. at throughput rates which are unattainable with the conventional columns, the average optimum theoretical plate height being about 20 mm.

EXAMPLE 8

A packing in accordance with FIG. 15 is employed in a gas scrubbing experiment. The column is 200 mm in diameter and packed to a level of 1000 mm. The hemispherical depressions in the packing plates have a diameter of 20 mm and the connecting holes have a diameter of 8 mm. Raschig rings (25 mm) are used for comparison.

Using the test system air/water for hydrodynamic testing and the system carbon dioxide/water/air to test scrubbing efficiency, it is found that pressure drops in the column in accordance with the invention are between 2 and 10 times lower. The column in accordance with the invention can take substantially higher liquid and gas loads before flooding occurs under all test conditions and the theoretical plate height is reduced by between 3 and 7 times.

Generally speaking, with packings in accordance with the invention the theoretical plate height can approach about one half the diameter of the individual cells of the porous medium. However, under practical operating conditions, the theoretical plate height is invariably increased somewhat by various inefficiency factors. The high separating efficiency observed even at very high throughput rates is surprising in view of the comparatively small surface area of the skeletal struts as compared with the void volume of the columns. A possible explanation may be the manner in which these skeletal struts repeatedly deflect the fluid phase flowing through the pores, inducing vortex formations and bringing about a swirling effect inside the cells before the fluid passes from one cell to the next. Also, the staggered pattern of the cells and connecting passages induces continuous transverse redistribution of the flowing phase.

In contrast to numerous conventional columns, the columns in accordance with the invention are largely insensitive to deviations in the plumbness of the column or to true horizontality of the column inserts. Accordingly the packings in accordance with the invention may be employed particularly advantageously on board seagoing vessels where nowadays small columns are used to fractionate at sea liquefied gases and where conventional columns cause problems when the vessel rolls or dips. Ordinary reticulated plastic foam may be employed particularly advantageously for the fractionation of sufficiently inert liquefied gases because of the low temperature thereof, the absence of crust-forming impurities and the low viscosity of the liquid phase.

We claim:

1. A packing which comprises a porous structure having essentially the texture of an open foam composed essentially of interleading pores and skeletal surfaces outlining the pores, the porous structure in cross-section extending essentially continuously, uniformly and at least predominantly coherently across its entire three dimensions;

wherein said porous structure is assembled by stacking a plurality of porous integral panels in which said texture repeatedly recurs in the two larger dimensions of each panel;

wherein the faces of each panel are formed essentially by a plurality of depressions, adjoining depressions of opposite panel faces being interleading when said panels are stacked, and adjoining depressions of the same panel face also being interleading when said panels are stacked; the shape of each depression being concave facing inward toward the adjoining depressions of the opposite panel;

wherein said adjoining opposed depressions form said pores when the panels are stacked; and wherein said depressions are arranged in a pattern essentially corresponding to the geometrical pattern of the peripheries of densely packed spheres;

whereby each of said pores formed by the opposed concave depressions is in interleading communication with each of the pores which immediately surround it; said communication being by means of passages between said pores; and said passages being located on the surface of each pore essentially at the corresponding points at which the surrounding spheres would contact each central sphere in a densely packed sphere geomtry.

2. The packing of claim 1, wherein said concave depressions have shapes which are essentially:

hemispherical to near-hemispherical;
square;
rhombic; or
pyramidal.

3. The packing of claim 2, wherein the shape of the concave depressions is essentially hemispherical.

4. The packing of claim 1, wherein said panels are stacked in immediate contact with one another.

5. The packing of claim 4, wherein the depressions of successive panels in stacked relationship are in matched relationship.

6. The packing of claim 5, wherein said concave depressions are essentially hemispherical in shape.

7. The packing of claim 4, wherein the depressions of successive panels are in staggered relationship.

8. The packing of claim 7, wherein said depressions are essentially hemispherical in shape.

9. The packing of claim 8, wherein the axes of said passages are perpendicular to the face of each panel.

10. The packing of claim 1, wherein said panels form a stack with gaps between successive panels.

11. The packing of claim 10, wherein said concave depressions are essentially hemispherical in shape and the depressions of successive panels in stacked relationship are in matched relationship.

12. The packing of claim 11, wherein the axes of said passages are perpendicular to the face of each panel.

13. The packing of claim 1, wherein the longitudinal axes of said passages extend radially from the center of each spherical pore.

14. The packing of claim 1, wherein the longitudinal axes of said passages are perpendicular to the face of each of said panels.

15. A packing body which provides skeletal surfaces suitable as contact areas between two interacting phases, at least one of which is fluid, and flow channels between the skeletal surfaces for said fluid phase, which comprises a porous structure wherein the pores are essentially spherical in shape and extend essentially continuously and coherently in three dimensions; wherein the pores have the geometry of densely packed spheres, each pore being in communication with each of the pores immediately surrounding it; said communication being by means of passages between said pores; and said passages being located on the surface of each pore essentially at the points at which the surrounding spheres contact each central sphere in the densely packed sphere geometry.

16. Packing bodies according to claim 15 assembled in a stack to form a packing of a column.

17. An apparatus for achieving mass transfer of mutually miscible substances between two fluid phases in intimate contact, in countercurrent, with one another, comprising:

(a) a separation space containing the packing of claim 1 having essentially the texture of an open pore foam composed of interleading pores and skeletal surfaces outlining the pores, the pores serving as flow channels for one of said fluid phases and the skeletal surfaces serving as carrier surfaces for the other of said fluid phases, being a liquid phase, the porous structure in cross-section extending essentially continuously, uniformly and at least predominantly coherently across said entire space, said skeletal surfaces being the essential contact area between said phases for the mass transfer of the mutually miscible substances;

(b) means adapted for introducing the fluid phases in countercurrent with one another and for introducing said mutually miscible substances into the space; and (c) outlet means adapted to withdraw from said space said fluid phases containing said mutually miscible substances.

18. A distribution separation process of the type in which a fluid phase flows relative to a second phase through a space having defined outlines and a separation takes place by material distribution between the phases which are intimately contacted with one another along the outside and both are confined to the outside of the solid surfaces of three-dimensionally interleading pores of a porous material composed of said pores and solid parts between the pores, the fluid phase being guided through the pores along a flow pattern directed by said solid surfaces, wherein said porous material is the packing of claim 1.

* * * * *